Figure 3:
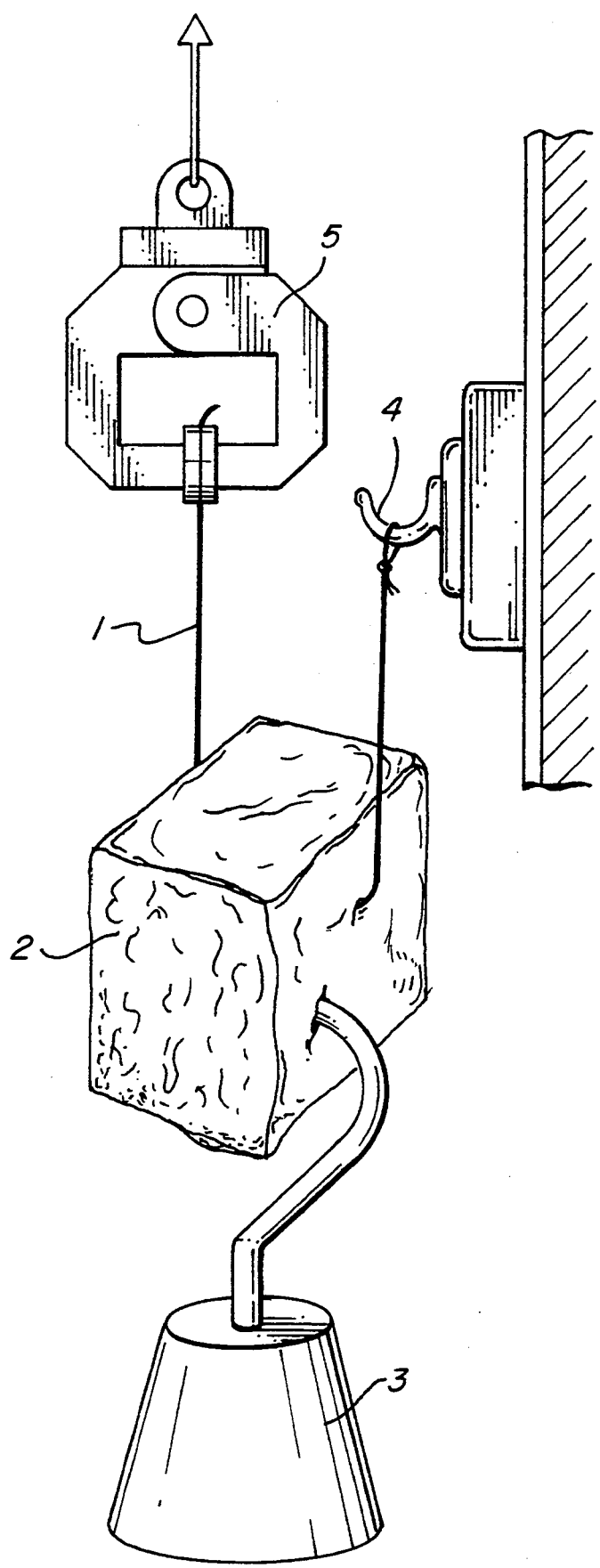

United States Patent
Jarrett et al.

[11] Patent Number: 5,352,515
[45] Date of Patent: Oct. 4, 1994

[54] COATING FOR TISSUE DRAG REDUCTION

[75] Inventors: Peter K. Jarrett, New Haven; George Jessup, Brookfield; Louis Rosati, Norwalk, all of Conn.; Chris Martin, Guildford, Australia; John W. Maney, Spring Valley, N.Y.

[73] Assignee: American Cyanamid Company, Wayne, N.J.

[21] Appl. No.: 843,053

[22] Filed: Mar. 2, 1992

[51] Int. Cl.⁵ .............. B32B 27/02; B32B 27/36; C08G 63/08; A61L 17/00
[52] U.S. Cl. .................... 428/357; 428/394; 428/395; 428/480; 525/408; 525/411; 525/415; 528/354; 606/230; 606/231
[58] Field of Search ............ 525/408, 411, 415; 528/354; 606/230, 231; 428/357, 394, 395, 480

[56] References Cited

U.S. PATENT DOCUMENTS

| | | | |
|---|---|---|---|
| 4,027,676 | 6/1977 | Mattei | 128/335.5 |
| 4,043,344 | 8/1977 | Landi et al. | 128/335.5 |
| 4,047,533 | 9/1977 | Perciaccante et al. | 128/335.5 |
| 4,201,216 | 5/1980 | Mattei | 128/335.5 |
| 4,438,253 | 3/1984 | Casey et al. | 528/86 |
| 4,452,973 | 6/1984 | Casey et al. | 528/354 |
| 4,459,317 | 7/1984 | Lambert | 427/2 |
| 4,526,938 | 7/1985 | Churchill et al. | 525/415 |
| 4,624,256 | 11/1986 | Messier et al. | 128/335.5 |
| 4,649,920 | 3/1987 | Rhum | 128/335.5 |
| 4,705,820 | 11/1987 | Wang et al. | 524/381 |
| 4,716,203 | 12/1987 | Casey et al. | 525/408 |
| 4,788,979 | 12/1988 | Jarrett et al. | 128/335.5 |
| 4,791,929 | 12/1988 | Jarrett et al. | 128/335.5 |
| 4,826,945 | 5/1989 | Cohen et al. | 528/76 |
| 4,857,602 | 8/1989 | Casey et al. | 525/408 |
| 4,942,035 | 7/1990 | Churchill et al. | 424/423 |
| 4,994,074 | 2/1991 | Bezwada et al. | 606/230 |
| 5,066,722 | 11/1991 | Tang et al. | 528/354 |
| 5,076,807 | 12/1991 | Bezwada et al. | 606/230 |
| 5,123,912 | 6/1992 | Kaplan et al. | 606/230 |

FOREIGN PATENT DOCUMENTS

| | | | |
|---|---|---|---|
| 014238 | 8/1980 | European Pat. Off. | A61K 9/02 |
| 411545 | 2/1991 | European Pat. Off. | A61L 17/00 |
| 436308 | 7/1991 | European Pat. Off. | A61L 17/00 |
| 1248513 | 10/1971 | United Kingdom | D06M 15/36 |

OTHER PUBLICATIONS

Synthesis and Characterization of Polyoxyethylene/-poly-E-caprolactone Block Copolymers. R. Perret and A. Skoulios; Makromol. Chem. 156, 143–156 (1972).
Synthesis and Characterization of Poly(oxyethylene)-poly-E-caprolactone Block Copolymers. Perret et al.; Chemical Abstract, vol. 7832x (1969).

Primary Examiner—John Kight, III
Assistant Examiner—Shelley A. Dodson
Attorney, Agent, or Firm—C. F. Costello, Jr.

[57] ABSTRACT

This invention relates to materials medical or veterinary use that possess considerably improved properties with regard to friction. The invention also relates to the production of such materials from existing materials that possess suitable bulk properties, but inappropriate frictional properties. This invention also relates to a hydrophilic coating material that provides improved frictional properties.

30 Claims, 6 Drawing Sheets

FIG. 1 (PRIOR ART)
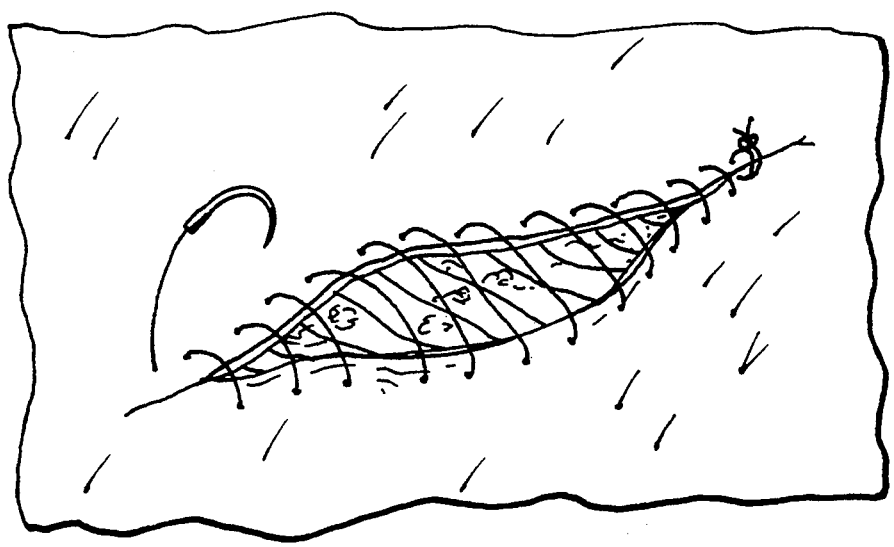
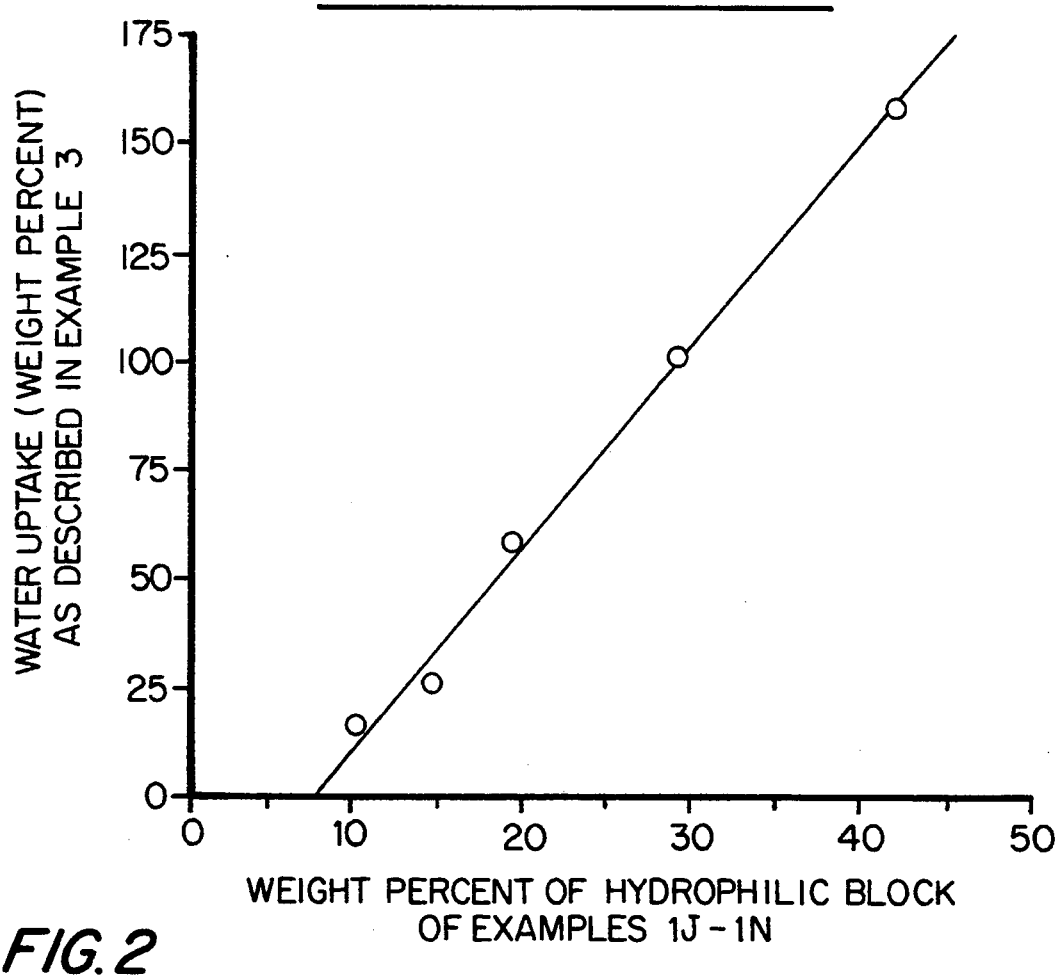
FIG. 2

COATING FOR TISSUE DRAG REDUCTION

BACKGROUND OF THE INVENTION

This invention relates to materials for medical or veterinary use that possess considerably improved properties with regard to friction. The invention also relates to the production of such materials from existing materials that possess suitable bulk properties, but inappropriate frictional properties. This invention also relates to a hydrophilic coating material that provides improved frictional properties.

In a particular aspect, the materials and method of this invention are useful for the fabrication of articles which contact the fluids or tissues humans or animals.

In a medical procedure the facile movement of a surface with respect to tissue is important in reducing damage to both the material of the surface and to the tissue. Damage to tissue as a result of "tissue drag" causes inflammation and pain to the person or animal and leads to a longer recovery time. High friction between the surface material and blood may result in clotting and subsequent occlusion of a blood vessel, for example with indwelling catheters. Friction may also damage the material, thus rendering it ineffective or shortening its useful life. The problem of "tissue drag" has been of concern to the medical and veterinary professions for some time.

Although friction may be reduced by the use of lubricating oils, such liquids are weakly associated with the surface of the material and will be removed upon repeated rubbing of the surface against the tissue, as in multiple loop suturing. The toxicity of the oils and their breakdown products are a major concern. The surfaces of this invention are an improvement over the existing art which uses these lubricating oils.

A number of patents describe the use of non-absorbable hydrophilic or hydrogel coatings which provide lubrication when wet. The coatings are disadvantageous due to the complex coating methods described. The multiple components of these coatings would also present serious toxicology concerns.

The frictional properties of solid polymers, metals or ceramics are strongly dependent on the chemical composition of the material surface. The tissue drag of medical or veterinary materials is a result of interfacial forces between the material and the tissue, and as a result is also affected by the composition of the material surface. A number of techniques known in the art are designed to effect a chemical change in the surface of materials and thereby alter the frictional properties of the surface. These techniques include corona discharge, flame treatment, acid etching, etc.

The present invention will be illustrated with respect to elastomeric sutures. It should be understood, however, that this in no way limits the scope of the invention. The method of the invention is equally useful for imparting low friction surfaces to catheters, pacemaker leads and other medical or veterinary products.

The utility of this invention is illustrated by the following analysis of suture properties as related to continuous vascular anastomosis: "The use of monofilament polypropylene (PROLENE ®-Ethicon) or monofilament polybutester (NOVAFIL ®-Davis and Geck) makes accurate anastomosis feasible, by allowing a number of suture loops to be placed with good vision prior to tightening of the suture to approximate the edges to be joined. Monofilament polypropylene (PROLENE ®) has long given excellent results in our experience. The particular advantage of this material is the ease with which the suture will pull through the tissues with minimal tissue drag. PROLENE ® is relatively stiff and even in fine anastomoses with 7/0 PROLENE ® there may be distortion of the anastomotic line. The recently available monofilament polybutester (NOVAFIL ®) has given excellent results in our practice and has shown improved handling characteristics—less 'memory' and stiffness making it an easier material to use. The suture is slightly elastic—this may have theoretical advantages in a pliant small vessel—and the reduced stiffness results in less distortion of fine anastomotic lines. When using the open technique, it is important to pull the suture tight after every two or three loops to avoid having loose loops in the anastomosis. This overcomes any problem that may be experienced with increased tissue resistance when using NOVAFIL ®." (From "Surgery of Coronary Artery Disease", D. J. Wheatley, ed., The C. V. Mosby Co., St. Louis, 1986.)

In certain procedures the surgeon, rather than tightening each suture loop individually may place multiple loose loops of suture in the tissue and then tighten the loops by pulling one or both ends (see FIG. 1). In vascular and other tissues, the two ends of tissue may be pulled together by pulling the suture ends, which is often referred to as the "parachute technique." The parachute technique is commonly used in suturing vascular tissue. Polypropylene is the most common suture material used for this technique. Techniques of this sort are advantageous since they provide benefits to the patient. Suture placement is more accurate since each end of tissue is better visualized. The technique is also faster and reduces the time until blood flow is restored.

Good slip of sutures through tissues is critical for applications such as vascular surgery. However, some currently available sutures such as polybutester tend to exhibit "stick-slip" behavior as they are pulled through tissue. These surfaces may initially move smoothly, but they then stick to the tissue and have to be pulled harder in order to continue the suturing process. The resulting oscillatory force may damage delicate vascular tissue. Sutures made from materials such as polypropylene do not show stick-slip behavior to the same extent as polybutester, but they are not sufficiently elastic for surgery on delicate tissue. A particular aspect of this invention overcomes the deficiencies of the prior art by disclosing a method for fabricating sutures which are highly elastic and have a low friction surface that avoids stick-slip behavior.

There is an advantage in using elastomeric sutures such as polybutester in cardiovascular surgery, in that an anastomosis (the sutured junction between two vessels) reflects more closely the natural compliance of the anatomical vessel. Such simulation of the properties of the natural vessel should help maintain long term patency of the anastomosis after surgery, in contrast to presently used non-elastic sutures which have high long term occlusion rates. A further advantage includes the superior ability of polybutester to maintain strength after gamma-ray sterilization as opposed to many other commonly used elastomeric sutures.

The stick-slip phenomenon is especially acute when either the suture or the tissue is elastic and when the suture is moving slowly. The problem is accentuated when there are multiple loops of the suture through the tissue (FIG. 1). To overcome this deficiency, the present invention provides a coating to the surface of known polymers. Similarly, these coatings can provide improved performance to metal or ceramic surfaces.

Accordingly, in one aspect, the present invention provides a novel, multilayer composite material with low tissue drag, the composite comprising a thin, polymeric surface layer and a bulk material of the required properties and form. The thin polymeric layer consists of a hydrophilic block copolymer suitable for contact with human or animal tissue.

In a second aspect, the invention provides a suture comprised of a multilayer composite material according to the first aspect of the present invention where the bulk material is an absorbable or nonabsorbable material suitable for suture applications. In a preferred case the suture is fabricated from an elastomeric material.

In a third aspect, the present invention provides a catheter comprising a polymeric article having a thin, polymeric surface layer and a bulk polymeric material, said surface layer providing hydrophilic material for contact with tissues or body fluids.

In yet a further aspect, the present invention provides a medical or veterinary implant with a low friction surface, said implant comprising a material wherein a surface of said materials bears a layer formed by coating the surface with a hydrophilic block copolymer. Such medical or veterinary implants could include absorbable or non-absorbable meshes, pins and screws for orthopedic surgery, vascular grafts, films for prevention of post-surgical adhesions, implants for joint lubrication. In some cases the entire implant could consist of the absorbable hydrophilic copolymers of the invention.

A number of hydrophobic absorbable coatings are disclosed in printed publications. These coatings were applied primarily for improvement of knot tying characteristics of multifilamentary sutures. The following U.S. Patents are illustrative: U.S. Pat. Nos. 4,791,929, 4,788,979, 4,705,820, 4,624,256, 4,201,216, and 4,994,074; and EP applications 436308, EP 411545, EP 376656.

One patent for improvement of knot tying characteristics contained a hydrophilic polymer component blended with two hydrophobic components (U.S. Pat. No. 4,027,676).

Several patents exemplify sutures with absorbable hydrophilic coatings for the primary purpose of improving knot tying characteristics: U.S. Pat. Nos. 4,857,602, 4,649,920, 4,047,533, 4,043,344. Two patents exemplify hydrophilic non-absorbable coatings to improve wettability and smoothness, GB 1248513, or to provide for controlled release of an anti-microbial agent, U.S. Pat. No. 4,875,479.

A number of patents disclose the use of non-absorbable hydrophilic coatings for medical articles for the purpose of lubrication: U.S. Pat. Nos. 5,041,100, 4,976,703, 4,961,954, 4,835,003, 4,801,475, 4,743,673, 4,729,914, 4,666,437, 4,589,873, 4,585,666, 4,487,808, 4,373,009, 4,100,309, 4,459,317, 4,487,808, and 4,729,914. Two additional published patent applications disclose hydrophilic lubricant coatings based on water soluble film forming polymers: EP 14238 and WO 8810284 A1.

Several patents disclose the preparation of synthetic absorbable hydrogel polymers. One of these patents, U.S. Pat. No. 4,716,203, discloses the use of a synthetic absorbable hydrogel polymer for the improvement of knot tying characteristics. The remaining patents describe the preparation of synthetic absorbable hydrogels: U.S. Pat. Nos. 4,942,035, 4,826,945, 4,526,938, 4,452,973, 4,438,253. These patents do not disclose the use of the exemplified materials as suture coatings for tissue drag reduction. It is not necessarily true that a hydrophilic or hydrogel polymers will perform well as a coating for tissue drag reduction, since the coating must possess the characteristics of low friction with tissue combined with good adherence as is demonstrated when friction does not increase as the material is repeatedly rubbed against tissue.

SUMMARY OF THE INVENTION

The following embodiments more fully describe the invention.

1. A block copolymer comprising a first block having a polyalkylene oxide and a second block having ε-caprolactone linkages, the improvement to the second block comprising linkages subject to hydrolytic degradation in-vivo being randomly configured with the ε-caprolactone linkages.

2. The copolymer of embodiment 1 wherein the first block is obtained by removing at least one terminal hydroxyl hydrogen from either a homopolymer of ethylene oxide or a copolymer of ethylene oxide and a cyclic ether, and reacting the homopolymer or copolymer with a monomer used to obtain said second block.

3. The copolymer of embodiment 2 wherein the cyclic ether is selected from the group consisting of

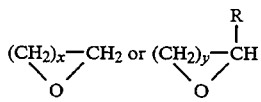

wherein x is 1 to about 9, y is 1 to about 9 and R is a $C_1$ to $C_6$ Alkyl group.

4. The copolymer of embodiment 2 wherein said first block is from about 5 to 95 percent by weight of said copolymer.

5. The copolymer of embodiment 4 wherein said first block is from about 20 to 60 percent by weight of said copolymer.

6. The copolymer of embodiment 5 wherein said first block is from about 25 to 45 percent.

7. The copolymer of claim 2 wherein the number average molecular weight of said first block is from about 4,000 to 30,000.

8. A bioabsorbable copolymer of embodiment 7 wherein the inherent viscosity of the copolymer, as measured at 30° C. for a 0.5% (w/v) solution in chloroform or methylene chloride, is 0.25 to about 1.50 dl/g.

9. A multiblock copolymer as in one of embodiments 1 to 7.

10. A triblock copolymer as in one of embodiments 1 to 7.

11. A diblock copolymer as in one of embodiments 1 to 7.

12. An ABA or AB block copolymer having a (B) block comprising a poly(alkylene oxide) having a number average molecular weight of about 5,000 to 20,000 and an A block comprising a biodegradable random copolymer of (1) the cyclic ester of an alpha-hydroxy acid and (2) ε-caprolactone, wherein the ABA or AB block polymer has a glass transition temperature at or less than 16° C.

13. An ABA block polymer according to embodiment 12 wherein the first cyclic ester is glycolide.

14. The polymer according to embodiment 13 wherein the B block is poly(ethylene oxide) or poly(ethylene oxide-co-propylene oxide).

15. The polymer according to embodiment 13 wherein the poly(alkylene oxide) comprises up to about 95 weight percent and the ratio of glycolide to ε-caprolactone components is within a range of about 5 weight percent glycolide and 95 weight percent ε-caprolactone to about 50 weight percent glycolide and 50 weight percent ε-caprolactone.

16. The polymer according to embodiment 15 wherein said ratio is within a range of about 60 to 90 weight percent ε-caprolactone.

17. The polymer according to embodiment 16 wherein said ratio is within a range of about 80 to 90 weight percent ε-caprolactone.

18. The polymer according to embodiment 17 wherein the ε-caprolactone component is about 85 weight percent.

19. The polymer according to embodiment 15 wherein said poly(alkylene oxide) comprises about 20 to 60 weight percent of the ABA polymer.

20. The polymer according to embodiment 19 wherein said polymer(alkylene oxide) comprises about 25 to 45 weight percent.

21. The polymer according to embodiment 15 wherein the number average molecular weight of said poly(alkylene oxide) is from about 6,000 to 20,000.

22. The polymer according to embodiment 21 wherein the said number average molecular weight of said poly(alkylene oxide) is up to about 14,000.

23. The polymer according to embodiment 22 wherein said number average molecular weight of said poly(alkylene oxide) is from about 8,000 to 14,000.

24. An AB block copolymer according to embodiment 12 wherein the first cyclic ester is glycolide.

25. The polymer according to embodiment wherein the B block is a monomethyl ether of a hydroxyl ended polyethylene oxide.

26. An article of manufacture comprising a lubricant, the lubricant manufactured from the copolymer as in one of embodiments 13 to 23.

27. An article of manufacture comprising a medical or surgical device coated with the lubricant of embodiment 26.

28. The article of embodiment 27 comprising a catheter.

29. The article of embodiment 27 comprising a surgical needle.

30. The article of embodiment 27 comprising a bone screw, pin or rod.

31. The article of embodiment 27 comprising a surgical clip or staple.

32. The article of embodiment 27 comprising a film.

33. An article of manufacture comprising a bioabsorbable film, or a knitted or woven mesh having a bioabsorbable coating, the bioabsorbable film or coating manufactured from a copolymer selected from the group consisting of a a) diblock copolymer having a first block comprising a polyalkylene oxide and a second block consisting essentially of aliphatic polyester linkages;

b) triblock copolymer having a middle block and two end blocks, the middle block obtained by removing both terminal hydroxyl hydrogens from either a homopolymer of ethylene oxide, or from a block or random copolymer of ethylene oxide and a cyclic ether, and each end block consisting essentially of aliphatic polyester linkages; and c) triblock copolymer having a middle block and two end blocks, the middle block obtained by removing both terminal hydroxyl hydrogens from a block or random copolymer of a first cyclic ether selected from the group consisting of

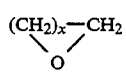

wherein x is 1 to about 9, and a second cyclic ether selected from the group consisting of

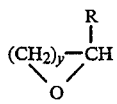

wherein y is 1 to about 9 and R is a $C_1$ to $C_6$ alkyl group, and each end block consisting essentially of aliphatic polyester linkages, said bioabsorbable film, or the knitted or woven mesh having said bioabsorbable coating useful as an adhesion prevention barrier for in-vivo mammalian tissue.

34. An article of manufacture comprising a surgical filamentary device having a bioabsorbable coating, the bioabsorbable coating manufactured from the copolymer as in one of embodiments 13 to 23.

35. The article of embodiment 34 wherein the surgical filamentary device is a suture or ligature.

36. The article of embodiment 35 wherein the suture or ligature is manufactured from a biocompatible polymer.

37. The article of embodiment 36 wherein the biocompatible polymer is selected from the group consisting of nylon, polybutester and polypropylene.

38. The article of embodiment 35 wherein the suture or ligature is a monofilament.

39. The article of embodiment 38 wherein said suture or ligature is manufactured from a polybutester.

40. The article of embodiment 35 wherein the suture or ligature is a multifilament.

41. The article of embodiment 40 wherein said suture or ligature is manufactured from a nonabsorbable polymer selected from the group consisting of polyester, nylon and silk.

42. The article of embodiment 34 wherein the surgical filamentary device is a knitted or woven mesh.

43. An article of manufacture comprising a bioabsorbable film, or a knitted or woven mesh having a bioabsorbable coating, the bioabsorbable film or coating manufactured from a copolymer selected from the group consisting of a a) diblock copolymer having a first block comprising a polyalkylene oxide and a second block having linkages prepared from monomers selected from the group consisting of lactides and 1,4-dioxane-2-one;

b) triblock copolymer having a middle block and two end blocks, the middle block obtained by removing both terminal hydroxyl hydrogens from either a homopolymer of ethylene oxide, or from a block or random copolymer of ethylene oxide and a cyclic ether, and each end block having linkages prepared from monomers selected from the group consisting of lactides and 1,4-dioxane-2-one; and c) triblock copolymer having a middle block and two end blocks, the middle block obtained by removing both terminal hydroxyl hydrogens from a block or random copolymer of a first cyclic ether selected from the group consisting of

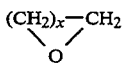

wherein x is 1 to about 9, and a second cyclic ether selected from the group consisting of

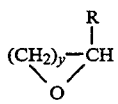

wherein y is 1 to about 9 and R is a $C_1$ to $C_6$ alkyl group, and each end block having linkages prepared from monomers selected from the group consisting of lactides and 1,4-dioxane-2-one, said bioabsorbable film, or the knitted or woven mesh having said bioabsorbable coating useful as an adhesion prevention barrier for mammalian tissue.

44. An article of manufacture comprising a bioabsorbable film, or a knitted or woven mesh having a bioabsorbable coating, the bioabsorbable film or coating manufactured from a copolymer selected from the group consisting of a a) diblock copolymer having a first block comprising a polyalkylene oxide and a second block consisting essentially of glycolic acid ester and trimethylene carbonate linkages;

b) triblock copolymer having a middle block and two end blocks, the middle block obtained by removing both terminal hydroxyl hydrogens from either a homopolymer of ethylene oxide, or from a block or random copolymer of ethylene oxide and a cyclic ether, and each end block consisting essentially of glycolic acid ester and trimethylene carbonate linkages; and c) triblock copolymer having a middle block and two end blocks, the middle block obtained by removing both terminal hydroxyl hydrogens from a block or random copolymer of a first cyclic ether selected from the group consisting of

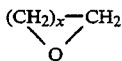

wherein x is 1 to about 9, and a second cyclic ether selected from the group consisting of

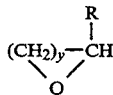

wherein y is 1 to about 9 and R is a $C_1$ to $C_6$ alkyl group, and each end block consisting essentially of glycolic acid ester and trimethylene carbonate linkages, said bioabsorbable film or the knitted or woven mesh having said bioabsorbable coating useful as an adhesion prevention barrier for in-vivo mammalian tissue.

45. An article of manufacture comprising a surgical suture or ligature having a bioabsorbable coating, the improvement comprising the bioabsorbable coating having a reduced tissue friction, the reduced tissue friction being at least about 10 percent less than an uncoated surgical suture or ligature, and remaining after about 2 to 20 passes through mammalian tissue having a thickness of up to about 2 cm.

46. The article of embodiment 45 wherein the reduced tissue friction is up to about 90 percent less than the uncoated surgical suture or ligature.

47. The article of embodiment 46 wherein the reduced tissue friction is at least about 20 up to about 80 percent less than said uncoated surgical suture or ligature.

48. The article of embodiment 47 wherein the reduced tissue friction is at least about 50 percent less than said uncoated surgical suture or ligature.

49. The article as in one of embodiments 45 to 48 wherein the reduced tissue friction remains after up to about 10 passes through mammalian tissue having a thickness of about 1 cm.

50. The article as in one of embodiments 45 to 48 wherein the suture or ligature is a monofilament.

51. The article of embodiment 50 wherein said suture or ligature is manufactured from a bioabsorbable polymer.

52. The article of embodiment 51 wherein the polymer is a homopolymer.

53. The article of embodiment 52 wherein the homopolymer is polydioxanone.

54. The article of embodiment 51 wherein the polymer is a copolymer.

55. The article of embodiment 54 wherein the copolymer comprises at least one glycolic acid ester linkage.

56. The article of embodiment 55 wherein the copolymer is polyglyconate.

57. A process for sterilizing the surgical filamentary device of embodiment 32 wherein said surgical filamentary device is manufactured from a nonabsorbable polymer selected from the group consisting of polybutester, polyester, nylon and silk, the process comprising:

packaging said suture or ligature in a sealed container that is impervious to microorganisms;

exposing the packaged suture or ligature to a gamma irradiation facility;

irradiating said packaged suture or ligature at at least about 1.5 Mrads; and removing the irradiated packaged suture or ligature from the gamma irradiation facility.

58. The process of embodiment 57 wherein the irradiating step is at least about 2.5 Mrads.

59. The process of embodiment 57 or 58 wherein the irradiating step is up to about 5 Mrads.

60. A method of closing a surgical opening in mammalian tissue comprising:

forming at least two loops adjacent to the mammalian tissue with a surgical suture having a bioabsorbable coating; and approximating said mammalian tissue by pulling on at least one end of the surgical suture.

61. The method of embodiment 60 wherein the approximating step is by pulling on both ends of said surgical suture.

62. The method of embodiments 60 or 61 wherein the forming and approximating steps comprise a surgical parachute technique.

63. The method of embodiment 62 wherein the forming step comprises up to about twenty loops adjacent to the mammalian tissue.

64. The method of embodiment 63 wherein the forming step comprises from about four to ten loops.

BRIEF DESCRIPTION OF THE ACCOMPANYING FIGURES

FIG. 1 shows multiple loops of an elastomeric suture through a wound. Such a technique may be used for many tissues, including vascular tissue.

FIG. 2-Graph of equilibrium water content of copolymer rods immersed in deionized water at 37° C.

FIG. 3 shows the apparatus used for measuring friction. A suture is passed through a piece of animal tissue (e.g. ovine aorta or myocardium, or cow tongue) to which a 100 g or 200 g weight is attached. One end of the suture is fixed, and the other end is attached to a force transducer. The force is measured as the suture moves through the tissue.

Figure 5:
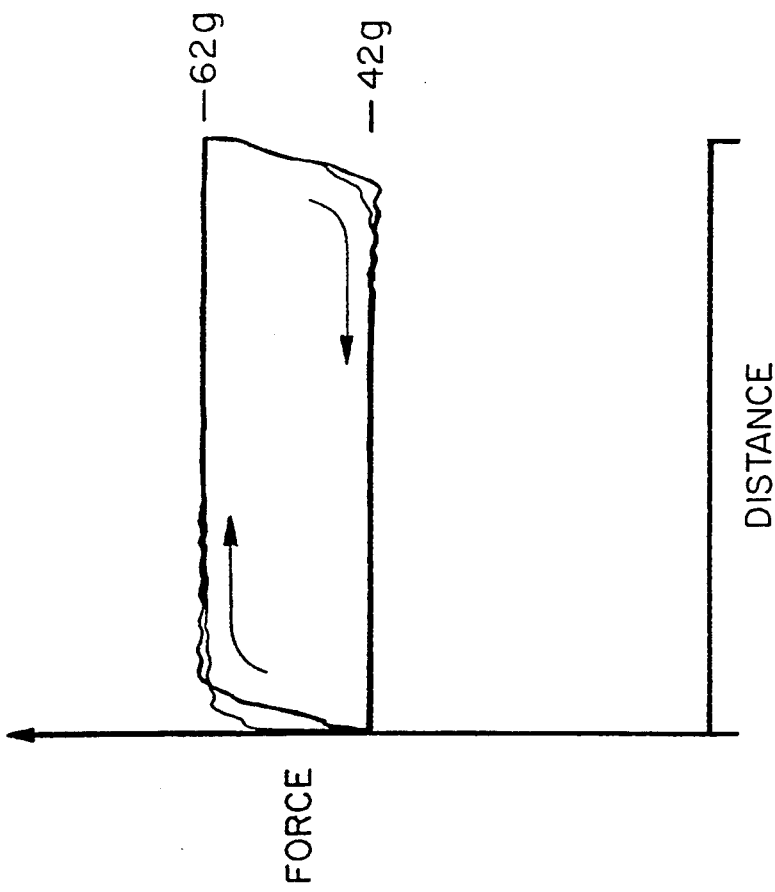
Figure 4:
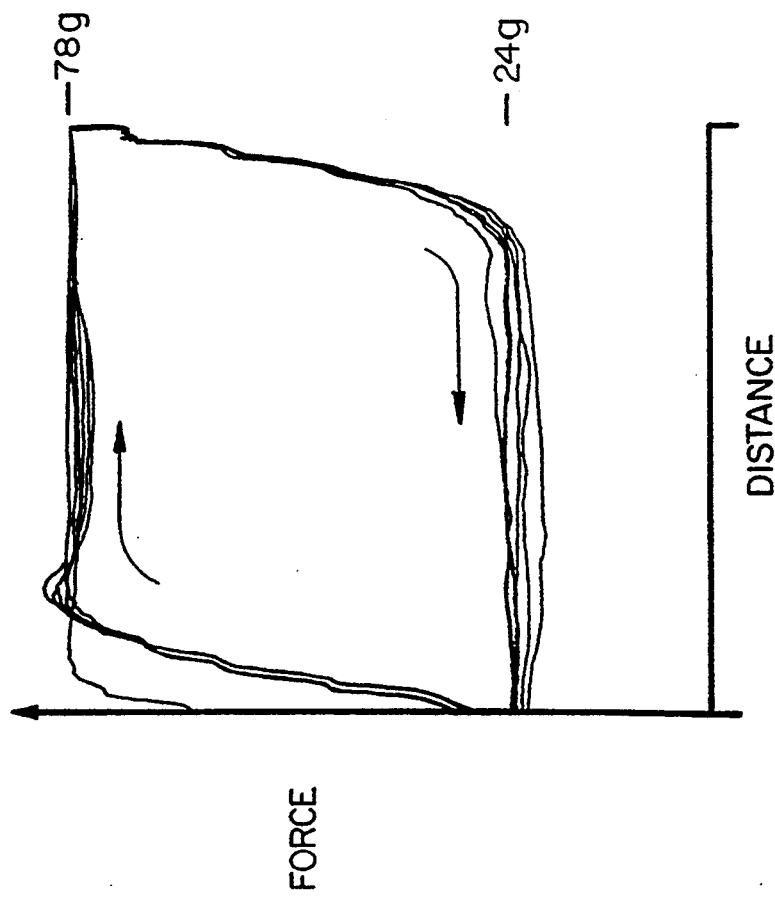

FIG. 4-Hysteresis-like curve from Instron testing machine tissue friction test of Size 6/0 polypropylene suture for comparison to FIG. 5 as described in Example 5.

FIG. 5-Hysteresis-like curve from Instron testing machine tissue friction test of Size 6/0 polybutester suture coated with the polymer known as example 1N (1 dip) as described in Example 5.

Figure 7:
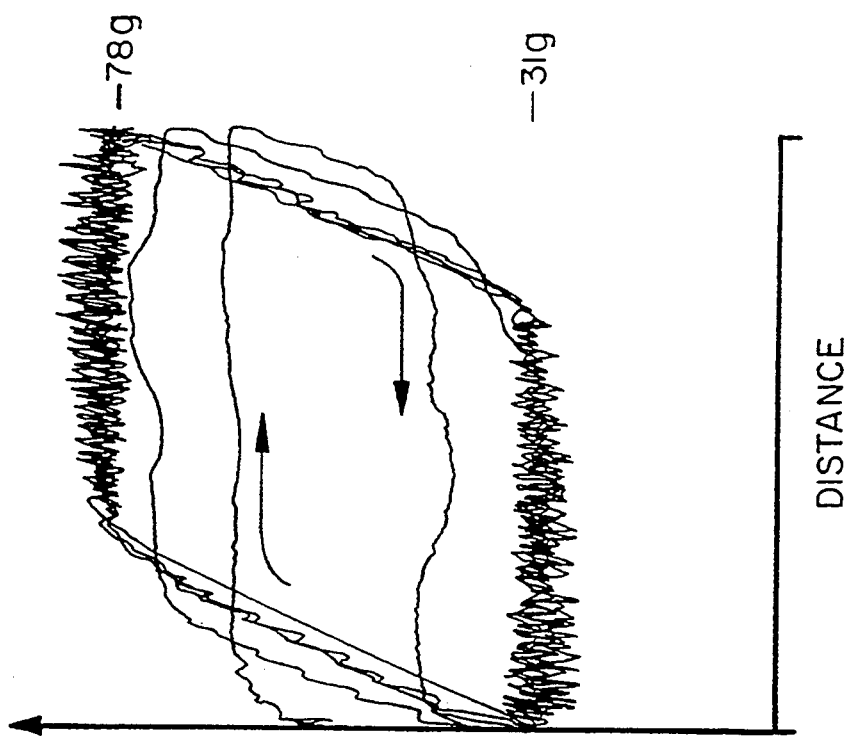
Figure 6:
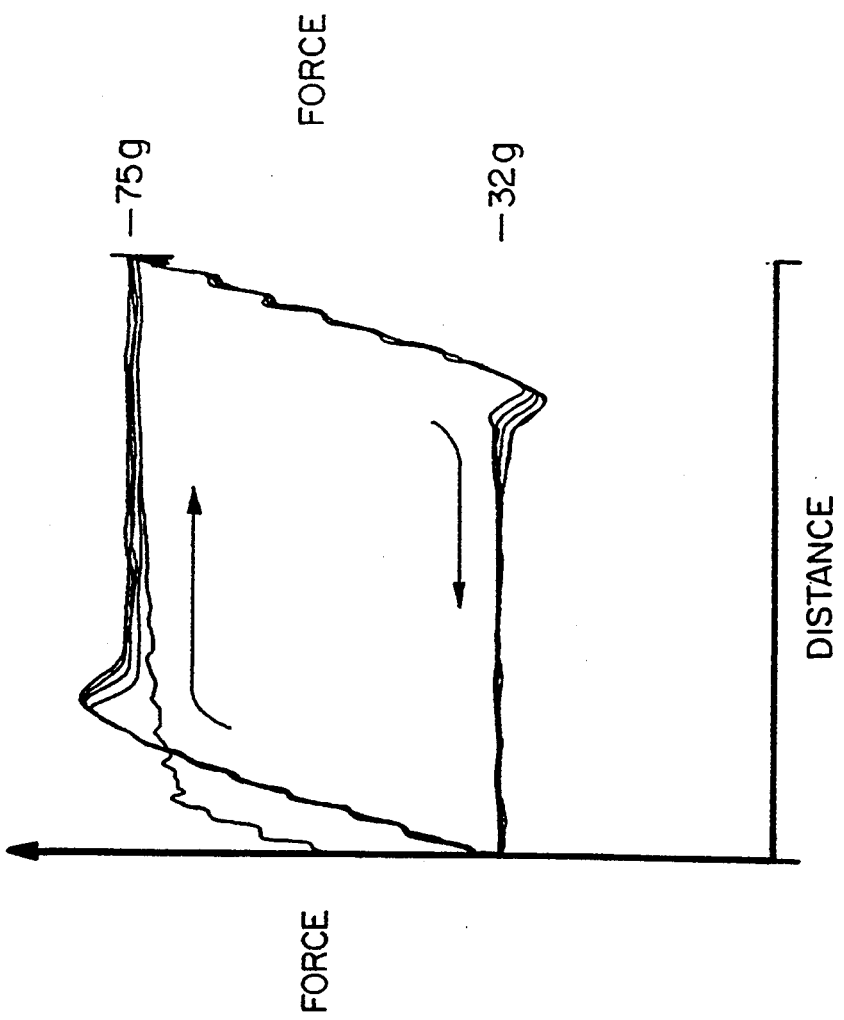

FIG. 6-Hysteresis-like curve from Instron testing machine tissue friction test of size 6/0 polypropylene suture for comparison to FIG. 7 as described in Example 5.

FIG. 7-Hysteresis-like curve from Instron testing machine tissue friction test of Size 6/0 polybutester suture coated with the polymer from example 1C (1 dip) as described in Example 5. This curve shows increased friction with repeated passes through tissue, indicating poor coating durability.

Figure 8:
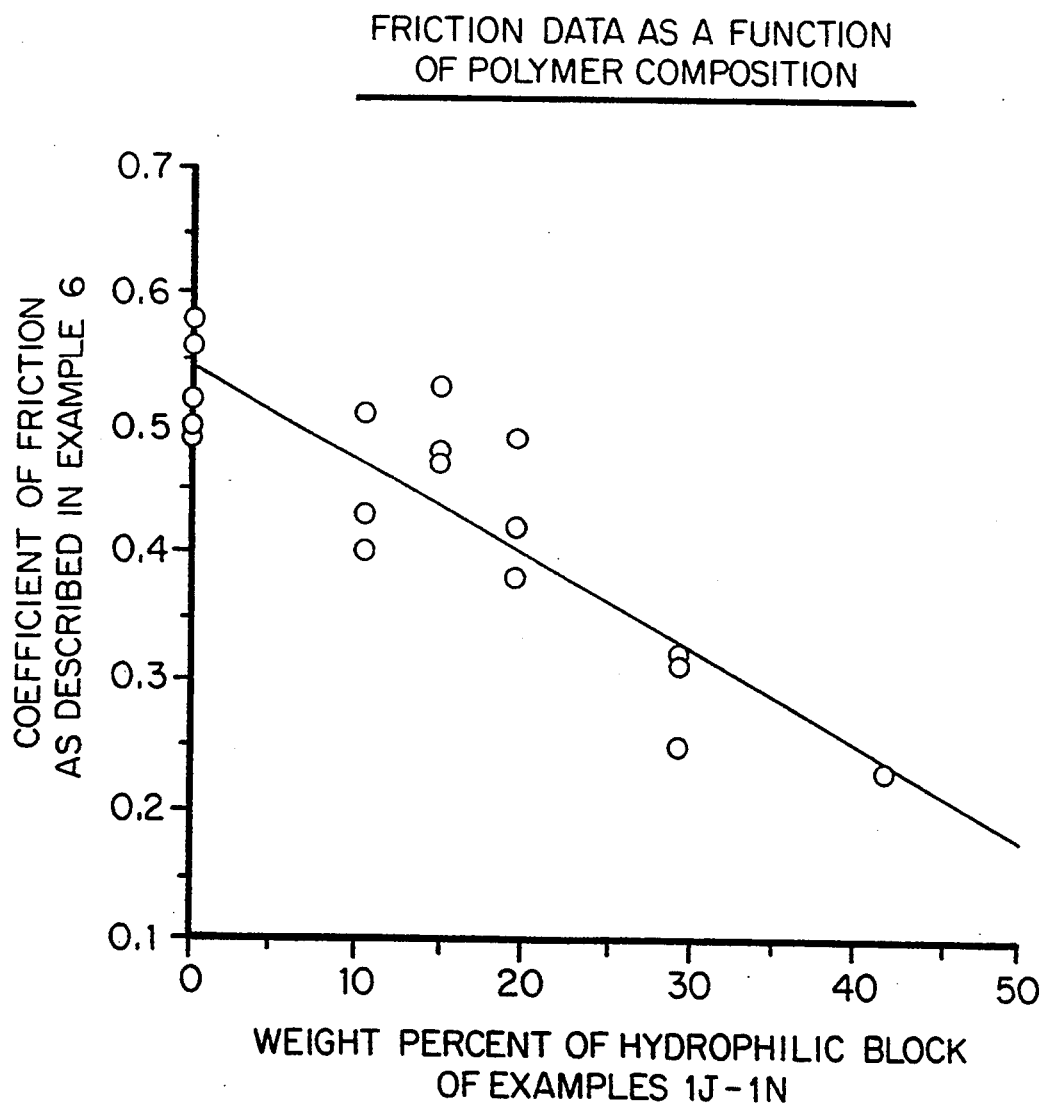

FIG. 8-Graph of coefficient at Friction measurements as described in Example 6 versus the weight percent of PLURONIC TM F-68 (BASF Wyandotte) incorporated in the coating copolymer for polybutester suture coated with copolymers 1J, 1K, 1L, 1M and 1N.

Figure 9:
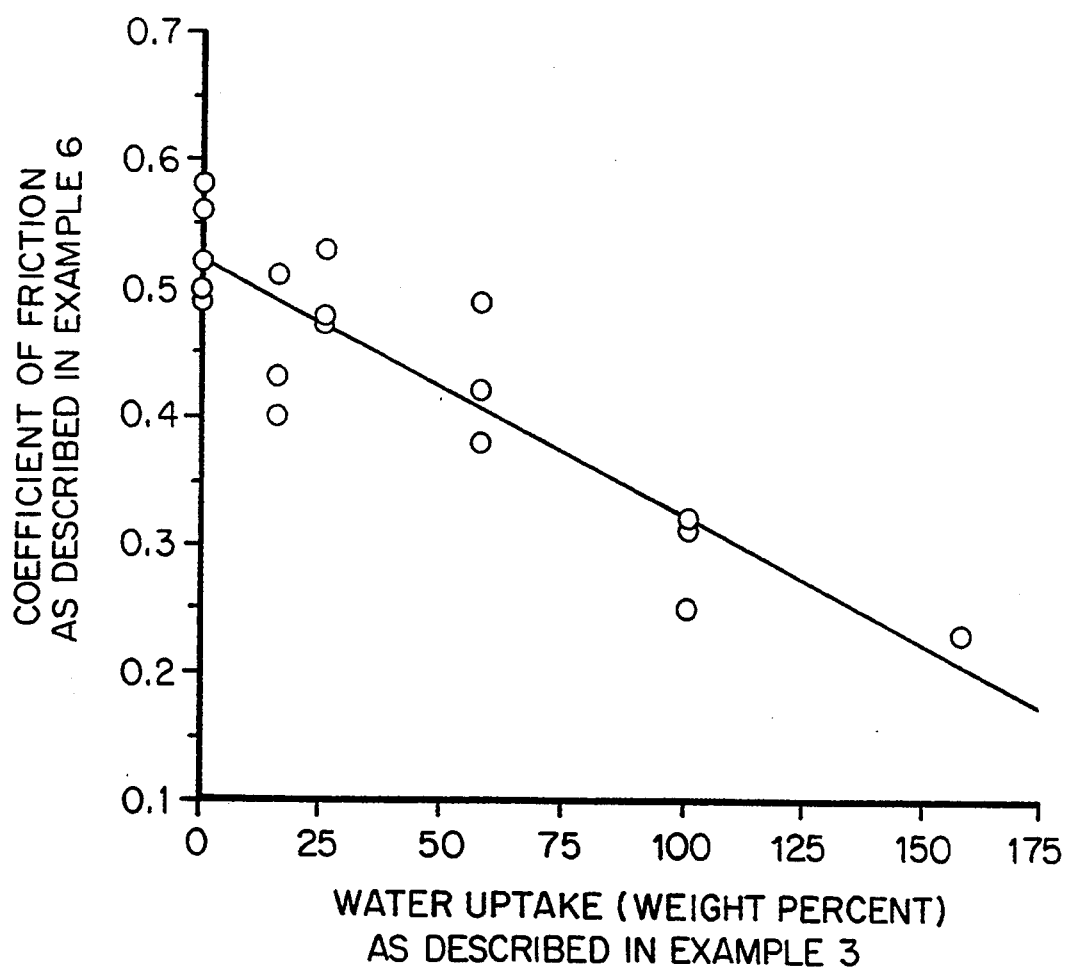

FIG. 9-Graph of coefficient of Friction measurements as described in Example 6 versus equilibrium water content (see Example 3) of coating copolymers for polybutester suture coated with copolymers from Examples 1J, 1K, 1L, 1M and 1N.

DESCRIPTION OF THE INVENTION

The sutures of this invention are composite structures in that they are multilayer materials fabricated by applying a thin layer onto a conventional material that serves as the bulk of the multilayer composite.

Novel elastomeric sutures provided by this invention are fabricated using a known material for the bulk material and applying a novel thin coating to the fiber made from the bulk material. The bulk material provides mechanical properties suitable to the application, while the novel thin layer must be stable with time and be capable of smooth passage through human or animal tissue. The multilayer structure of the invention permits independent optimization of bulk and tissue response properties.

This invention also provides a process for the production of said elastomeric sutures. The process comprise the application of a hydrophilic block copolymer to the surface of said elastomeric sutures by contacting said sutures with a solution consisting of a volatile solvent e.g. acetone, ethyl acetate, methylene chloride, methyl ethyl ketone (MEK), and a quantity of said hydrophilic block copolymer. The volatile solvent is allowed to evaporate, leaving a composite structure comprising the bulk polymeric material and a thin layer of said hydrophilic block copolymer.

Any one of the known materials such as polybutester, polypropylene, silk, catgut, nylon, polyglycolic acid, polyglyconate, stainless steel, cotton, etc. may be used for the bulk material because the process of this invention can proceed without regard for the composition of the bulk material, with the exception that the adhesion of the coating to the surface of the bulk material is affected by the compatibility of the coating copolymers with the bulk material surface. The invention is particularly applicable to polymeric materials which have inadequate frictional properties with tissue, but have useful mechanical properties. For vascular surgery the preferred bulk material is polybutester due to its elastomeric properties.

In another aspect, this invention provides metallic and inorganic materials modified by the process of this invention in order to equip them with a low friction polymer coating, for example suture needles.

As a suture or suture-needle coating, the hydrophilic block copolymer coating can be absorbable or nonabsorbable. In certain cases it may be desirable that the hydrophobic block of the copolymer be nonabsorbable where long term surface hydrophilicity is needed. It may also be advantageous to provide a non-absorbable coating with an absorbable overcoating to provide for short term lubricity as well as specific long term surface properties. Since in certain cases, such as sutures, the reduction of friction between the suture material and tissue is required only during the surgical procedure, and since the compatibility of the bulk material with tissue is well established for the commercial sutures of interest, the preferred coating is an absorbable hydrophilic block copolymer. Absorbable coatings are also advantageous since they would present no long term risks should they be ablated during the surgical procedure.

The absorbable block copolymers exemplified in this invention consist of at least one hydrophilic block and at least one hydrophobic block. Said hydrophobic blocks are hydrolyzable under in-vivo conditions. The term "hydrophobic blocks", as used in describing this invention, refers to blocks that are not normally water soluble and absorb relatively low amounts of water, i.e. less than 10% by weight. The hydrophilic blocks, when not covalently bound to the hydrolyzable hydrophobic blocks are normally capable of being dissolved by body fluids. When covalently bound to the hydrophilic block, the hydrolyzable hydrophobic block provides a mechanism for retaining the hydrophilic block on the surface of the bulk material for the required period of time. The hydrolyzable hydrophobic block provides sufficient compatibility with the bulk material surface to resist ablation and diminution of lubricating properties during the surgical procedure. The chemical composition selected for the hydrolyzable hydrophobic block depends on the chemical nature of the bulk material surface and must be designed to provide adequate adhesion between the coating and the bulk material. A further advantage of this invention is the flexibility of design of the hydrolyzable hydrophobic block. The proper design of the hydrolyzable hydrophobic block eliminates the need for chemical modification of the bulk material surface as is often required in prior-art coating systems to provide adequate adhesion of a coating to a bulk material.

The hydrolyzable hydrophobic blocks of the current invention can be homopolymers or copolymers formed from monomers selected from the group consisting of: ε-caprolactone, glycolide, 1-lactide, d,1-lactide, d-lactide, meso-lactide, trimethylene carbonate, 4,4-dimethyl-1,3-dioxan-2-one, p-dioxanone, dioxepanone, δ-valerolactone, β-butyrolactone, ε-decalactone, 2,5-diketomorpholine, pivalolactone, α,α-diethylpropiolactone, 6,8-dioxabicyclooctan-7-one, ethylene carbonate, ethylene oxalate, 3-methyl-1,4-dioxane-2,5-dione, 3,3-dimethyl-1,4-dioxane-2,5-dione, and other subtituted glycolides, and substituted lactides. Other cyclic esters described in the art can also be employed within the scope of this invention.

The hydrophilic blocks of the current invention can be selected from the group consisting of: polyvinylalcohol, polyvinylpyrrolidone, polyoxyethylene, polyacrylamide, poly(2-hydroxy-ethylmethacrylate), polymethacrylamide, dextran, alginic acid, sodium alginate, polysaccharides, gelatine and copolymers of two or more of the monomers from which the above polymers are derived and polyoxyethylene/polyoxypropylene block copolymers. Other hydrophilic polymers described in the art that contain hydroxyl groups capable of reacting with the monomers of the hydrolyzable hydrophobic blocks can also be employed within the scope of this invention. The methods of preparation of the hydrophilic block copolymers of this invention are known in the prior art.

In a preferred embodiment of the hydrophilic block copolymer of this invention, the hydrophilic blocks are comprised of polyoxyethylene or polyoxyethylene/polyoxypropylene block copolymers, and the hydrolyzable hydrophobic blocks are comprised of a copolymer of ε-caprolactone and glycolide and the substrate suture material is polybutester.

In another preferred embodiment of the hydrophilic block copolymer of this invention the hydrophilic blocks are comprised of polyoxyethylene or polyoxyethylene/polyoxypropylene copolymer, and the hydrolyzable hydrophobic block is comprised of a copolymer of glycolide and trimethylene carbonate and the substrate suture material is polyglyconate.

Measurement of Frictional Properties

Frictional tests using sheep aorta or myocardium or cow tongue provide a convenient assay of tissue drag. Such studies are also directly relevant to medical or veterinary applications in contrast to tests done with steel surfaces or rubber. It is considered that the surface treatment procedures suitable for the reduction of friction in animal tissue are also appropriate for the optimization of sutures for general surgery.

Other aspects of the present invention, and modifications and variations thereto, will become apparent to those skilled in the art on reading this invention, and all such other aspects and modifications and variations are to be considered to be included within the scope of the present invention.

EXAMPLES

Example 1: Preparation of Coating Polymers

Purification of Polyethylene Glycol (Polyoxyethylene) or PLURONIC ™ F-68 (Polyoxyethylene/polyoxypropylene block copolymer from BASF Wyandotte):

The material to be purified is dissolved in methanol at a concentration of 10% w/v. The solution is then freed of residues by slowly passing the solution through a methanol conditioned mixed bed anionic and cationic exchange resin (TMD8, Alcoa Separations Technology Inc., IL, U.S.A.). The methanol is then removed on a rotary evaporator. Prior to polymerization, the desired amount of purified diol is dried in a vacuum oven for 18 hours at 90° C. and <1 mm Hg.

Polymer Synthesis:

The desired amounts of cyclic ester or carbonate monomer(s) and polyethylene glycol or PLURONIC ®F-68 were charged to a flask and melted under nitrogen. Catalyst was then added and the contents were charged to a heated, nitrogen purged reactor. The mixture is stirred at the polymerization temperature for a specified period of time. The polymer was discharged from the reactor and dried in a vacuum oven for 18 hours at 70°-80° C. and <1 mm Hg. Specific examples of polymers produced by this procedure are given in Table 1.

Example 2

ε-Caprolactone/trimethylene carbonate/polyethylene glycol pentablock polymer

Purified polyethylene glycol, 8000 molecular weight, (PEG 8000, 10.00 g), trimethylene carbonate, (TMC, 27.00 g), and stannous octoate (3.3 mg, 0.001 mole percent based on TMC plus ε-Caprolactone) were melted together under nitrogen. The mixture was charged to a preheated, nitrogen purged stirred reactor. The contents were stirred at 185° C. for 4 hours 30 minutes. ε-Caprolactone (Cap 63.00 g) was then charged to the reactor and the contents were stirred at 185° C. for an additional 1 hour 25 minutes. The polymer was discharged from the reactor and dried in a vacuum oven for 18 hours at 75° C. and <1 mm Hg. The polymer had an inherent viscosity of 1.12 dL/g in chloroform at 30° C. at a concentration of 0.5 g/dL. The composition was 66.9/23.0/10.1 weight percent Cap/TMC/PEO as measured by 1H-NMR spectroscopy.

Example 3

Water Uptake of Various Coating Polymers

Water uptake experiments were carried out on injection molded rods with a diameter of ⅛" and a length of 1-2 cm. These rods were fabricated from polymers from Example 1. The samples were immersed in deionized water or phosphate buffered saline at pH 7.4. Periodically a sample was removed, wiped free of surface moisture and weighed. This was continued until an equilibrium weight was obtained. Equilibrium water content values are summarized in Table 2. In cases where the sample became badly fragmented as a result of swelling, the moisture content was determined by weight loss after drying. The data for water uptake is

TABLE 1

| Example | Polyalkylene oxide[A] (g) | Endblocks[B] (g) | Catalyst[C] mg (mole %) | Polymerization Temp (C.) | Polymerization Time (hr:min) | Polymer Composition[B,E] (weight percent) | IV[F] (solvent) |
|---|---|---|---|---|---|---|---|
| 1A | PEG 8000 (22.50) | Gly/TMC (136.69/65.81) | 7.3 (0.001) | 185 | 5:30 | (Gly/TMC/PEO (64.7/24.8/10.5) | 0.64 (HFAS) |
| 1B | PEG 8000 (60.00) | Gly/TMC (94.50/45.50) | 5.1 (0.001) | 185 | 4:03 | Gly/TMC/PEO (52.2/14.8/33.0) | 0.68 (HFAS) |
| 1C | PEG 8000 (22.30) | Gly/TMC (121.50/81.00) | 37.2 (0.005) | 190 | 1:54 | Gly/TMC/PEO (55.6/34.2/10.2) | 0.47 (CHCl3) |
| 1D | PEG 14000 (22.30) | Gly/TMC (121.50/81.00) | 37.2 (0.005) | 190 | 2:00 | Gly/TMC/PEO (56.7/33.1/10.2) | 0.49 (CHCl3) |
| 1E | PEG 14000 (50.00) | Gly/TMC (120.00/80.00) | 20.9 (0.005) | 185 | 4:15 | Gly/TMC/PEO (48.8/30.0/21.2) | 0.37 (CHCl3) |
| 1F | PEG 14000 (32.00) | Gly/TMC (42.00/28.00) | 12.9 (0.005) | 185 | 0:58 | Gly/TMC/PEO (48.0/17.3/34.7) | 0.47 (HFAS) |
| 1G | PEG 8000 (25.00) | Cap/Gly (191.25/33.75) | 55.8 (0.007) | 180 | 4:30 | Cap/Gly/PEO (75.8/13.9/10.3) | 1.07 (CHCl3) |
| 1H | PEG 8000 (30.00) | Cap/Gly (59.50/10.50) | 17.3 (0.007) | 180 | 4:30 | Cap/Gly/PEO (56.4/11.1/32.5) | 0.54 (CHCl3) |
| 1J | F-68 (25.00) | Cap/Gly (191.25/33.75) | 55.8 (0.007) | 180 | 4:30 | Cap/Gly/F-68 (75.9/13.8/10.3) | 1.08 (CHCl3) |
| 1K | F-68 (37.50) | Cap/Gly (180.62/37.50) | 52.6 (0.007) | 180 | 4:30 | Cap/Gly/F-68 (72.2/13.0/14.8) | 0.89 (CHCl3) |
| 1L | F-68 (50.00) | Cap/Gly (170.00/30.00) | 49.6 (0.007) | 180 | 4:30 | Cap/Gly/F-68 (67.5/13.0/19.5) | 0.76 (CHCl3) |
| 1M | F-68 (30.00) | Cap/Gly (59.50/10.50) | 17.3 (0.007) | 180 | 4:30 | Cap/Gly/F-68 (60.6/10.3/29.1) | 0.56 (CHCl3) |
| 1N | F-68 (40.00) | Cap/Gly (51.00/9.00) | 14.9 (0.007) | 180 | 4:30 | Cap/Gly/F-68 (47.8/10.3/41.9) | 0.46 (CHCl3) |
| 1O | PEG 8000 (30.00) | Cap (70.00) | 17.4 (0.007) | 180 | 5:00 | Cap/PEO (67.3/32.7) | 0.63 (CHCl3) |
| 1P | PEG 14000 (40.00) | TMC (160.00) | 17.7[D] (0.005) | 180 | 1:20 | TMC/PEO (79.2/20.8) | 0.84 (CHCl3) |
| 1Q | PEG 8000 (30.00) | TMC (70.00) | 13.9 (0.005) | 180 | 3:00 | TMC/PEO (66.9/33.1) | 0.61 (CHCl3) |
| 1R | PEG 8000 (20.00) | dl-Lac/TMC (108.00/72.00) | 29.7 (0.005) | 185 | 3:20 | dl-Lac/TMC/PEO (58.6/31.6/9.8) | 0.59 (CHCl3) |
| 1S | PEG 8000 (30.00) | dl-Lac/TMC (42.00/28.00) | 14.9 (0.006) | 185 | 2:28 | dl-Lac/TMC/PEO (41.1/26.0/32.9) | 0.49 (CHCl3) |
| 1T | PEG 8000 (20.00) | Gly/dl-Lac (60.4/139.6) | 17.4 (0.005) | 185 | 2:25 | Gly/dl-Lac/PEO (29.0/61.4/9.6) | 0.96 (CHCl3) |
| 1U | PEG 8000 (30.00) | Gly/dl-Lac (21.14/48.86) | 10.6 (0.005) | 185 | 2:15 | Gly/dl-Lac/PEO (21.9/46.4/31.7) | 0.50 (CHCl3) |

[A]PEG = Polyethylene Glycol, the number is the stated molecular weight Pluronic F-68 (BASF), a poly(ethylene oxide/propylene oxide) copolymer.
[B]Gly = Glycolide
dl-Lac = dl-Lactide
TMC = Trimethylene carbonate
Cap = epsilon-Caprolactone
PEO = polyethylene oxide.
F-68 = Pluronic F-68
[C]Catalyst = stannous octoate.
[D]Catalyst = stannous chloride dihydrate.
[E]Determined by 1H-NMR spectroscopy.
[F]Inherent Viscosity, measured at 30° C., polymer concentration = 0.5 g/dL.

summarized in Table 2. Water uptake data for Examples 1J, 1K, 1L, 1M and 1N are shown graphically in FIG. 2.

Example 4

Coating Procedure

Polymer samples from Example 1 were dissolved at a 5 g/dL concentration in acetone (or in methylene chloride if the polymers were not acetone soluble). Coatings were applied to polybutester sutures by hand-dipping lengths of size 6/0 polybutester sutures in the solutions. The hand-dipping procedure consisted of passing the suture through the solution by pulling one end of the strand while holding a portion of the strand in the solution using a ceramic guide rod with a grooved tip. Up to three passes through the solution were used to apply coatings of increasing thickness. The actual coating level was not measured.

TABLE 2

| Polymer from Example Number | Water Uptake Temperature (C.) | Swelling Medium | EWC[A] |
|---|---|---|---|
| 1A | RT | DI H2O | 126 |
| 1G | RT | DI H2O | 20 |
|  | 37 | DI H2O | 24 |
| 1J | RT | DI H2O | 14 |
|  | 37 | DI H2O | 16 |
| 1K | RT | DI H2O | 24 |
|  | 37 | DI H2O | 26 |
| 1L | RT | DI H2O | 71 |
|  | 37 | DI H2O | 58 |
|  | RT | PBS | 48 |
|  | 37 | PBS | 41 |
| 1M | 37 | DI H2O | 101 |
| 1N | 37 | DI H2O | 158 |

[A]Equilibrium water content = 100 * (wt. hydrated − wt. dry)/(wt. dry). See Example 3.

Example 5

Tissue Drag Measurement

Tissue drag was determined by measuring the force required to draw a suture through a piece of cow tongue using an Instron testing machine. Suture specimens were prepared as described in Example 4. All samples in this Example were size 6/0 and had the same size needle. Coated polybutester sutures had a TE-1 needle and an uncoated comparison polypropylene suture (PROLENE ®) had the closest equivalent needle (C-1). A small piece of cow tongue was cut into approximately a 1 cm cube. The tongue was kept moistened at all times with Dulbecco's Phosphate Buffered Saline (Cat. No. 310-4190 AK). A 100 g weight was attached to the tongue cube. The needle was then passed through the tissue. One end of of the suture was affixed to a stationary clamp on the Instron machine. The other end of the suture was clamped to the load cell, so that the tissue and the attached weight hung free. FIG. 3 shows a schematic of the apparatus for measuring tissue drag. The Instron was set to cycle five times over a 3.5" distance at a speed of 10 inches/minute. A full scale load of 200 grams was used and the data was collected on a strip chart recorder with a chart speed of 10 inches/minute. The strip chart was also set to cycle with the Instron crosshead to produce a "hysteresis-like curve" with forces associated with the ascending and descending crosshead movement.

To interpret the data, the difference between the average maximum (ascending crosshead) force and average minimum (descending crosshead) force was calculated. Four specimens of each suture sample were tested using the same tissue cube. An uncoated comparison suture (PROLENE ® polypropylene suture with a C-1 needle) was then tested in the same manner. The values for the force differences of the four test specimens were averaged and divided by the force difference for the comparison suture and a relative value was determined. This value was called the "Friction Index". Samples with more frictional resistance than the comparison suture had friction index values greater than 1, and those with lower frictional resistance than the comparison suture had friction index values less than 1. FIGS. 4 and 5 show typical strip chart traces for the polypropylene comparison sample and for polybutester coated with the polymer from example 1N. See Table 3 for the Friction Index results of this testing. Some of the Friction Index values in Table 3 appear to show an increase with increased coating level (more dips). This increase may be due to increased surface roughness (or unevenness) of the thicker coatings.

FIGS. 6 and 7 show strip chart traces for a polypropylene comparison suture and polybutester coated with the polymer from Example 1C, respectively. The force difference in FIG. 7 increased with successive passes through the tissue due to ablation of the coating. The reported values for friction index for such cases was calculated using the final force difference.

Example 6

Coefficient of Friction

Tissue drag was also determined by measuring the force required to draw a suture through a piece of sheep heart muscle using an Instron testing machine. The heart tissue was taken from the left ventricular wall. The tissue was kept moist throughout the experiment with 0.9 g/dL NaCl/H₂O solution. The test procedure was similar to that described in Example 5 with the exceptions that an eyed needle (Davis & Geck TS-2, 41 cm) was used rather than an attached needle and the attached weight was 200 g. In this example, the coefficient of friction ($\mu$) was calculated using the following formula:

$$\mu = F/N$$

where

F = ascending force − descending force
N = ascending force + descending force

In this test, the value for $\mu$ was determined for each cycle of the test (a cycle is defined as one ascending pass and one descending pass) and a total of three cycles was run for each sample.

This test was used to study the effect of the degree of hydrophilicity on the coefficient of friction of the coated suture. Samples containing PLURONIC ® F-68 (F-68) as the hydrophilic block—samples 1J, 1K, 1L, 1M and 1N—were used in this example. The degree of hydrophilicity was determined in two ways: the percent of F-68 (see Example 1) and the equilibrium moisture uptake (see Example 3). The relationships of $\mu$ versus the F-68 content of the coating polymers and versus the water uptake of the coating polymers are shown graphically in FIGS. 8 and 9 for coating polymers 1J through 1N. In these graphs, the values plotted for 0% F-68 and 0% water uptake are the values for uncoated polybutester. If a copolymer of the composition of the hydrolyzable hydrophobic block were used for the 0% F-68 data point, the value for coefficient of friction would not be expected to be significantly less than uncoated polybutester. Also, the value for the coefficient of friction for sample 1N was calculated from data obtained using the Example 5 method. Higher concentrations of F-68 would be more hydrophilic than

TABLE 3

| Example | Friction Index Testing Results | | |
|---|---|---|---|
| | Solvent[A] | No. Dips[B] | Friction Index[C] |
| Uncoated | | | 1.290 |
| 1C | M | 1 | 1.048 |
| | | 2 | 1.105 |
| | | 3 | 1.270 |
| 1D | M | 1 | 1.224 |
| | | 3 | 1.148 |
| 1M | A | 1 | 0.684 |
| | | 2 | 0.703 |
| | | 3 | 0.870 |
| 1N | A | 1 | 0.500 |
| | | 3 | 0.468 |
| 1H | A | 1 | 0.484 |
| | | 3 | 0.441 |
| 1O | A | 1 | 1.145 |
| | | 3 | 1.145 |
| 1P | A | 1 | 1.366 |
| | | 3 | 1.295 |
| 1Q | A | 1 | 0.812 |
| | | 3 | 1.001 |
| 1R | A | 1 | 0.804 |
| | | 2 | 1.033 |
| | | 3 | 1.200 |
| 1S | A | 1 | 1.014 |
| | | 2 | 1.096 |
| | | 3 | 1.200 |
| 1T | A | 1 | 1.120 |
| | | 2 | 1.091 |
| | | 3 | 1.160 |
| 1U | A | 1 | 1.048 |
| | | 2 | 1.124 |
| | | 3 | 1.310 |
| 2 | A | 1 | 1.240 |

TABLE 3-continued

| Friction Index Testing Results | | | |
|---|---|---|---|
| Example | Solvent[A] | No. Dips[B] | Friction Index[C] |
| | | 3 | 1.044 |

[A]M = Methylene Chloride, A = Acetone
[B]Number of times the suture was dipped, see example 4
[C]See example 5 for explanation of friction index the coatings in FIGS. 8 and 9, and may provide superior lubricity, but higher F-68 levels may result in the loss of coating durability. A coating of pure F-68 would be expected to be quickly removed from the suture surface after contacting the moist tissue.

Example 7

Effect of substrate on coating durability

The tissue drag method described in Example 6 was used to measure the effect of substrate on the durability of the coating. The coefficient of friction of uncoated size 6/0 polyglyconate using the method described in Example 6 was 0.5. Large stick-slip oscillations were observed. The same lot of size 6/0 polyglyconate was coated with the copolymer from Example 1C (3 dips, methylene chloride solution) as described in Example 4. This coated polyglyconate suture was tested for tissue friction using the method described in Example 6. The coefficient of friction was 0.10, no "stick-slip" oscillations were observed. As a test of coating durability, a section of suture was re-tested a total of 13 times. No increase in coefficient of friction and no "stick-slip" was observed in the repeated tests (with coefficient of friction values ranging from 0.12 to 0.09). This demonstrates excellent coating durability of the Example 1C copolymer on polyglyconate. In contrast, the Example 1C copolymer was found to exhibit poor durability when coated onto polybutester, as shown in FIG. 7 and described in Example 5. Coating durability is therefore controlled by proper matching of coating and substrate.

Example 8

Radiation Effect on Tissue Drag

Size 6/0 polybutester suture was coated with the polymer from Example 1M. The samples were coated from a 3.5 g/dL acetone solution using a capillary coating machine. The coating level was 0.35% by weight, measured gravimetrically after stripping off the coating with acetone. Test sutures were made by cutting the fiber to length and attaching TE-1 needles. Some of the samples were then packaged and sterilized by γ-irradiation at 2.5 Mrad as is done for commercial NOVAFIL® suture. Other samples were packaged, but not sterilized. Tissue drag was measured for both sterile and nonsterile samples as described in Example 5. The friction index values were 0.83 for the non-sterile and 0.85 for the sterile suture. This is not considered a significant difference in friction index.

Example 9

Adhesion Prevention Film Evaluation

Polymer from Example 1A was used to prepare a film using a vacuum heat press. The press conditions were 145° C., 28 in. Hg vacuum, platen pressure was 30 psi for 3 min. and 250 psi for 3 additional min. The resulting film was annealed for 24 hours at 60° C. in a convection oven. The film was cut into 1 in.×2 in.×0.003 in. samples. The film samples were sealed in foil laminate suture envelopes and sterilized by gamma-irradiation (2.5 Mrad).

The surgical study was done using twelve rats, eight male and four female, ranging in weight from 360 to 670 grams. The rats were placed under general anesthesia and prepared for aseptic surgery. A midline laparotomy was done. The left abdominal side-wall was reflected and an area of about 2 cm×2 cm of the peritoneum and underlying muscle was abraded and scraped using a #10 surgical blade. The cecum was exteriorized and a similar size area of the serosa was abraded using a dry surgical sponge. Two size 3-0 silk sutures were tied about 1 cm apart through the cecal wall near the center of the serosal injury. In the CONTROL animals, the injured cecum and silk sutures were fixed in close contact with the injured abdominal side wall by suturing the cecum to the side-wall peritoneum using two size 4-0 DEXON "S" sutures, one placed proximally and one distally to the areas of injury. In the TEST animals, the film was sutured to the abdominal wall over the area of injury using a 4-0 DEXON "S" suture at each of the four corners, and the cecum then brought in contact as described above.

The rats were individually housed in stainless steel cages and provided water and food at all times. All survived and appeared to be in good health when sacrificed 28 days postoperative.

The system used to grade adhesions is shown in Table 4. Adhesions were scored using a blind method where the evaluator did not know which of the two groups the individual rat was from.

The results (Table 5) show a significant reduction in the number and severity of surgical adhesions when the film made from the absorbable hydrophilic block copolymer of Example 1A is used as a temporary barrier.

TABLE 4

| Adhesion Grading System | |
|---|---|
| Characteristic | Score |
| Attachment (neo-connective tissue attachment connecting primary tissues) | |
| No attachments | 0 |
| Wide plane attaching primary tissues | 1 |
| Narrow plane attaching primary tissues | 2 |
| Primary tissues closely attached with indistinct or no plane between. | 3 |
| Extent* | |
| (% Involvement) | |
| None | 0 |
| < 25% | 1 |
| > 25% < 50% | 2 |
| > 50% < 75% | 3 |
| > 75% | 4 |
| Type* | |
| None | 0 |
| Filmy, no vessels (transparent) | 1 |
| Opaque, no vessels (translucent) | 2 |
| Opaque, small vessels present grossly | 3 |
| Opaque, larger vessels present grossly | 4 |
| Tenacity* | |
| None | 0 |
| Adhesions essentially fell apart | 1 |
| Adhesions lysed with traction | 2 |
| Adhesions required sharp dissection for lysis | 3 |

TABLE 5

ADHESION RESULTS IN RATS WITH EXAMPLE 1A FILM

| Sample | Sex | Weight (Gms) Op | Weight (Gms) Sac | Attachment | Extent | Type | Tenacity |
|---|---|---|---|---|---|---|---|
| TEST | | | | | | | |
| 9a | M | 450 | 467 | 0 | 0 | 0 | 0 |
| 9b | M | 490 | 521 | 0 | 0 | 0 | 0 |
| 9c | M | 480 | 488 | 0 | 0 | 0 | 0 |
| 9d | F | 360 | 375 | 1 | 2 | 3 | 1 |
| 9e* | F | 430 | 416 | 3 | 4 | 3 | 3 |
| 9f | F | 395 | 408 | 1 | 1 | 2 | 2 |
| CONTROL | | | | | | | |
| | M | 450 | 470 | 2 | 4 | 3 | 2 |
| | M | 550 | 587 | 2 | 4 | 3 | 3 |
| | M | 470 | 499 | 2 | 4 | 2 | 3 |
| | F | 349 | 340 | 2 | 4 | 2 | 3 |
| | M | 780 | 662 | 3 | 4 | 3 | 3 |
| | M | 670 | 661 | 2 | 4 | 3 | 2 |

*Cecal wall tore and contents spilled during surgery.

We claim:

1. An article of manufacture comprising a surgical filamentary device having a bioabsorbable coating, the bioabsorbable coating manufactured from an ABA or AB block copolymer having a B block comprising a poly(alkylene oxide) having a number average molecular weight of about 5,000 to 20,000 and an A block comprising a biodegradable random copolymer of (1) glycolide and (2) ε-caprolactone, wherein the ABA or AB block polymer has a glass transition temperature at or less than 16° C.

2. The article according to claim 1 wherein the B block is poly(ethylene oxide) or poly(ethylene oxide-co-propylene oxide).

3. The article according to claim 1 wherein the poly(alkylene oxide) comprises up to about 95 weight percent and the ratio of glycolide to ε-caprolactone components is within a range of about 5 weight percent glycolide and 95 weight percent ε-caprolactone to about 50 weight percent glycolide and 50 weight percent ε-caprolactone.

4. The article according to claim 3 wherein said ratio is within a range of about 60 to 90 weight percent ε-caprolactone.

5. The article according to claim 4 wherein said ratio is within a range of about 80 to 90 weight percent ε-caprolactone.

6. The article according to claim 5 wherein the ε-caprolactone component is about 85 weight percent.

7. The article according to claim 2 wherein said poly(alkylene oxide) comprises about 20 to 60 weight percent of the ABA polymer.

8. The article according to claim 7 wherein said polymer(alkylene oxide) comprises about 25 to 45 weight percent.

9. The article according to claim 2 wherein the number average molecular weight of said poly(alkylene oxide) is from about 6,000 to 20,000.

10. The article according to claim 9 wherein the said number average molecular weight of said poly(alkylene oxide) is up to about 14,000.

11. The article according to claim 10 wherein said number average molecular weight of said poly(alkylene oxide) is from about 8,000 to 14,000.

12. The article of claim 1 wherein the surgical filamentary device is a suture or ligature.

13. The article of claim 12 wherein the suture or ligature is manufactured from a biocompatible polymer.

14. The article of claim 13 wherein the biocompatible polymer is selected from the group consisting of nylon, polybutester and polypropylene.

15. The article of claim 12 wherein the suture or ligature is a monofilament.

16. The article of claim 15 wherein said suture or ligature is manufactured from a polybutester.

17. The article of claim 12 wherein the suture or ligature is a multifilament.

18. The article of claim 17 wherein said suture or ligature is manufactured from a nonabsorbable polymer selected from the group consisting of polyester, nylon and silk.

19. The article of claim 1 wherein the surgical filamentary device is a knitted or woven mesh.

20. A medical or surgical film having a bioabsorbable coating, the bioabsorbable coating consisting essentially of an ABA or AB block copolymer having a B block comprising a poly(alkylene oxide) having a number average molecular weight of about 5,000 to 20,000 and an A block comprising a biodegradable random copolymer of (1) glycolide and (2) ε-caprolactone, wherein the ABA or AB block polymer has a glass transition temperature at or less than 16° C.

21. The film according to claim 20 wherein the B block is poly(ethylene oxide) or poly(ethylene oxide-co-propylene oxide).

22. The film according to claim 20 wherein the poly(alkylene oxide) comprises up to about 95 weight percent and the ratio of glycolide to ε-caprolactone components is within a range of about 5 weight percent glycolide and 95 weight percent ε-caprolactone to about 50 weight percent glycolide and 50 weight percent ε-caprolactone.

23. The film according to claim 22 wherein said ratio is within a range of about 60 to 90 weight percent ε-caprolactone.

24. The film according to claim 23 wherein said ratio is within a range of about 80 to 90 weight percent ε-caprolactone.

25. The film according to claim 24 wherein the ε-caprolactone component is about 85 weight percent.

26. The film according to claim 22 wherein said poly(alkylene oxide) comprises about 20 to 60 weight percent of the ABA polymer.

27. The film according to claim 26 wherein said poly(alkylene oxide) comprises about 25 to 40 weight percent.

28. The film according to claim 22 wherein the number average molecular weight of said poly(alkylene oxide) is from about 6,000 to 20,000.

29. The film according to claim 28 wherein the said number average molecular weight of said poly(alkylene oxide) is up to about 14,000.

30. The film according to claim 29 wherein said number average molecular weight of said poly(alkylene oxide) is from about 8,000 to 14,000.

* * * * *